(12) United States Patent
Wong

(10) Patent No.: US 7,469,475 B2
(45) Date of Patent: Dec. 30, 2008

(54) SAFE KNIFE SHEATH

(76) Inventor: Wai Yip Wong, Flat B, 11/Fl., Block 6, Classical Garden II, Tai Po, New Territories, Hong Kong (CN)

( * ) Notice: Subject to any disclaimer, the term of this patent is extended or adjusted under 35 U.S.C. 154(b) by 36 days.

(21) Appl. No.: 10/509,153

(22) PCT Filed: Mar. 28, 2002

(86) PCT No.: PCT/CN02/00213
§ 371 (c)(1),
(2), (4) Date: Sep. 28, 2004

(87) PCT Pub. No.: WO03/082532
PCT Pub. Date: Oct. 9, 2003

(65) Prior Publication Data
US 2005/0204565 A1    Sep. 22, 2005

(51) Int. Cl.
*B26B 29/02* (2006.01)
*B26B 3/06* (2006.01)

(52) U.S. Cl. .............. 30/156; 30/162; 30/151

(58) Field of Classification Search .......... 30/138, 30/143, 151, 162; 76/86, 82; 242/232–234; 224/242, 234; D22/118; D3/220; 451/555
See application file for complete search history.

(56) References Cited

U.S. PATENT DOCUMENTS

| | | | | |
|---|---|---|---|---|
| 2,793,434 A * | 5/1957 | Wigington | .................. | 30/151 |
| 3,676,961 A * | 7/1972 | Jackson | ...................... | 451/555 |
| 3,774,350 A * | 11/1973 | Bayly | .......................... | 451/540 |
| 4,091,691 A * | 5/1978 | Bayly | ............................. | 76/86 |
| 4,277,888 A * | 7/1981 | Szabo | ........................ | 30/162 |
| 4,523,379 A * | 6/1985 | Osterhout et al. | ............ | 30/151 |
| 4,654,968 A * | 4/1987 | Gatley et al. | .................. | 30/138 |
| 5,009,040 A * | 4/1991 | Petroff | ....................... | 451/555 |
| 5,092,046 A * | 3/1992 | Collins | ........................ | 30/162 |
| 5,784,786 A * | 7/1998 | Williams | ..................... | 30/138 |
| 5,915,793 A * | 6/1999 | Serpa | .......................... | 30/162 |
| 6,117,002 A * | 9/2000 | Stokes et al. | ................ | 451/555 |
| 6,138,363 A * | 10/2000 | Kawashima | ................. | 30/151 |
| 2003/0079351 A1* | 5/2003 | Davis | .......................... | 30/200 |

* cited by examiner

*Primary Examiner*—Boyer D. Ashley
*Assistant Examiner*—Laura M. Lee

(57) ABSTRACT

A safe knife sheath comprising a sheath body is mounted inside the sheath body movable in a sliding motion and a movable blade support. The front part of the sheath body has a push button, the lower part of which is connected to a positioning element. A positioning groove corresponding to the positioning element is disposed in the lower part of the blade support. A positioning channel is disposed inside the sheath body on the top. A positioning lobe corresponding to the positioning channel is disposed on the top of the blade support. A first reset spring is connected to the top of the push button at one end, and the other end of which is fixed in the upper end of the sheath body. A trapezoidal piece is disposed in the back of the blade support. A second reset spring is disposed on the lower side of the trapezoidal piece. One end of the second reset spring is fixed in the lower end of the sheath body and the other end is fixed on the inner side of the sheath body.

6 Claims, 4 Drawing Sheets

SAFE KNIFE SHEATH

BACKGROUND OF THE INVENTION

The present invention relates to knife sheaths and more particularly pertains to an improved knife sheath which is convenient to use and is safe from accidental injury when pulling the knife out of the sheath.

Knives are indispensable to the daily life of people. There is a wide variety of knives, such as folding knives and straight knives, which are portable and convenient to use while traveling. In comparison, straight knives are structurally more stable and reliable, and require less effort and are more convenient to use. However, straight knives are not that portable in the sense that they must be carried in sheaths so as to prevent personal injury caused by improper placing or fetching. The ordinary type of knife sheaths in common use is of relatively simple structure with only a sheath body. When a knife is inserted into the sheath body and placed in a bag, the knife may be released from the sheath without being noticed and thus the cutting edge of the knife blade may very easily cause accidental injury.

There is also another type of knife sheaths which has a sheath body comprising at least an outer sheath body and an inner sheath body. The knife is first inserted into the inner sheath body, and then the inner sheath body is inserted into the outer sheath body. This type of knife sheaths is complex in structure and is inconvenient to use and carry. When the knife is inserted into the sheath after rinsing, water from the knife easily accumulates inside the enclosed sheath. Owing to the poor ventilation inside the sheath, the knife blade is prone to rusting, which would shorten the service life of the knife.

The foregoing structures of knife sheaths all have the risks of causing accidental injury to the hand holding the sheath while the other hand pulling the knife out of the sheath.

BRIEF SUMMARY OF THE INVENTION

In view of the aforesaid disadvantages now present in the prior art, the present invention provides a safe knife sheath that is easy to carry, safe to use, convenient to clean and capable of preventing the knife from rusting easily.

To attain this, the present invention generally comprises a sheath body and a blade support. The blade support is mounted inside the sheath body movable in a sliding motion. The front part of the sheath body has a push button. A positioning element is connected to the lower part of the push button. A positioning groove corresponding to the positioning element is disposed in the lower part of the blade support. A positioning channel is disposed inside the sheath body on the top. A positioning lobe corresponding to the positioning channel is disposed on the top of the blade support. A first reset spring is connected to the top of the push button at one end, and the other end of which is fixed in the upper end of the sheath body. A trapezoidal piece is disposed in the back of the blade support. A second reset spring is disposed on the lower side of the trapezoidal piece. One end of the second reset spring is fixed in the lower end of the sheath body and the other end is fixed on the inner side of the sheath body.

The safe knife sheath is characterized by that the lower part of the positioning element is in a wedge-like shape.

The safe knife sheath is characterized by that the positioning groove comprises a locating piece and a guiding piece with a wedge-like surface, and the locating piece is disposed in the lower part of the blade support in position corresponding to the opening of the sheath body, and the guiding piece with the wedge-like surface is disposed in the middle lower part of the blade support.

The safe knife sheath is characterized by that a semi-circular notch is disposed in the rear part of the sheath body, and the semi-circular notch is disposed in the middle of the opening of the sheath body.

The safe knife sheath Is characterized by that a plurality of holes is perforated in the front part of the sheath body.

The safe knife sheath is characterized by that the plurality of holes is elongated.

It is an object of the present invention to provide a safe knife sheath which can lock the knife in the sheath by means of connecting the push button device with the positioning element, thereby avoiding the danger of injury as when the knife is released from the sheath accidentally and facilitating ease of carrying, thus overcoming the disadvantages of the prior art.

It is another object of the present invention to provide a safe knife sheath which can retain the cutting edge of the knife in the blade support by the application of the movable blade support, thereby avoiding injury to the hand holding the sheath while the other hand pulling out the knife, thus overcoming the disadvantages of the prior art.

It is a further object of the present invention to provide a safe knife sheath with a movable blade support which can move in and out in a sliding motion and so the knife sheath is safe, reliable, easy to carry and convenient to use and clean.

An even further object of the present invention is to provide a safe knife sheath with a plurality of holes thereon which allows good ventilation and speedy drying up of water shedding into the sheath from the knife after rinsing, thereby making the knife less susceptible of rusting and extending the service life of the knife, thus overcoming the disadvantages of the prior art.

DETAILED DESCRIPTION OF THE INVENTION

The present invention is capable of the embodiment described below.

Figure 1:
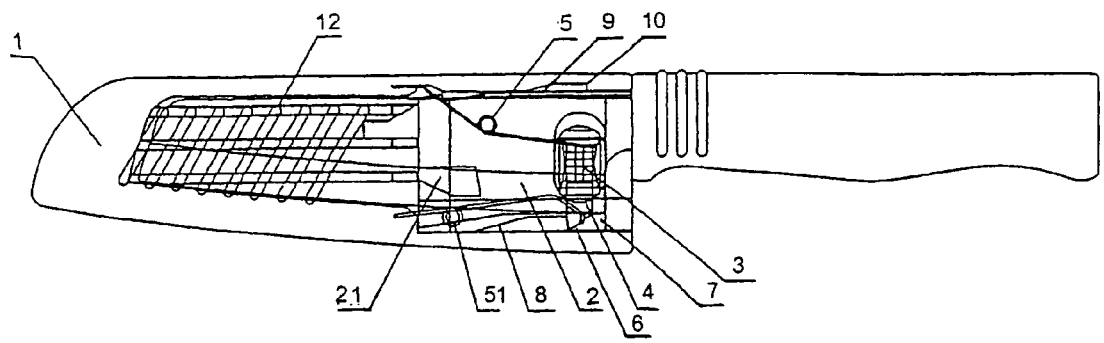
FIG. 1 is a schematic view of the present invention.

As illustrated in FIG. 1, the present prevention comprises a sheath body 1, a blade support 2 and a push button 3. The push button 3 is disposed near the opening of the sheath body 1, and a positioning element 4 is connected to the lower part of the push button 3. The lower part of the positioning element 4 is in a wedge-like shape. A positioning groove 6 corresponding to the positioning element 4 is disposed in the lower part of the blade support 2. The positioning groove 6 comprises a locating piece 7 and a guiding piece 8 with a wedge-like surface. The locating piece 7 is disposed in the lower part of the blade support 2 at the opening. The guiding piece 8 with the wedge-like surface is disposed in the middle lower part of the blade support 2. A positioning lobe 10 is disposed on the top of the blade support 2. A positioning channel 9 corresponding to the positioning lobe 10 is disposed inside the sheath body 1 on the top. A first reset spring 5 is connected to the top of the push button 3 at one end, and the other end of the first reset spring 5 is fixed in the upper end of the sheath body 1. A trapezoidal piece 21 is attached to a position where the back of the blade support 2 connects the middle lower end of the sheath body 1. A second reset spring 51 is disposed on the lower side of the trapezoidal piece 21. One end of the second reset spring 51 is fixed in the lower end of the sheath body 1 and the other end is fixed on the inner side of the sheath body 1. A plurality of holes 12 is perforated in the sheath body 1.

Figure 2:
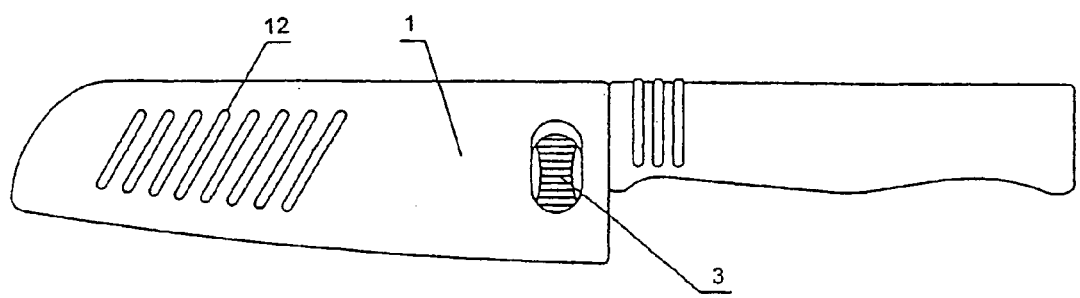
FIG. 2 is a perspective view of the present invention.

As illustrated in FIG. 2, a plurality of elongated holes 12 is perforated in the front end of the sheath body 1, which improves the ventilation inside the sheath body 1, so that when the knife has been rinsed and put into the sheath body 1, water shedding into the sheath body 1 from the knife can quickly dry off, and thus avoiding rusting of the knife.

Figure 3:
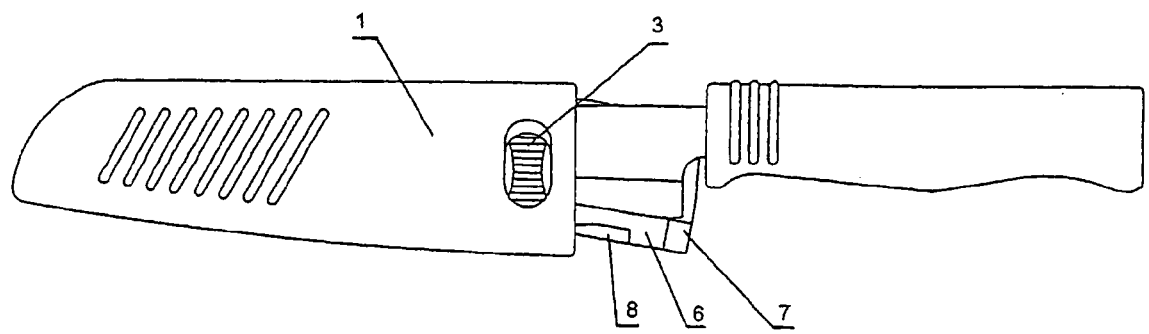
FIG. 3 is a perspective view of the present invention with the knife being partly pulled out.
Figure 4:
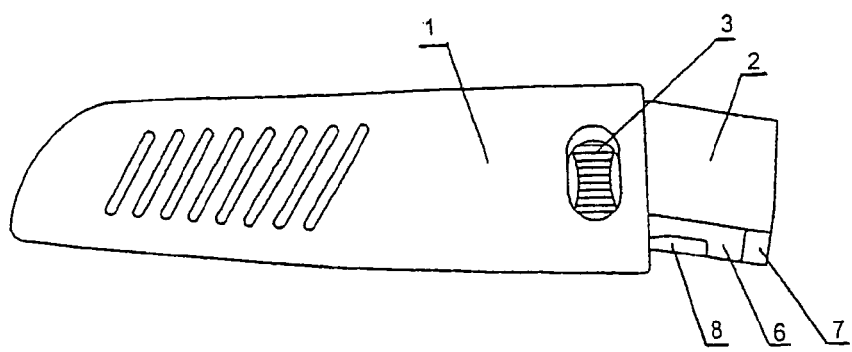
FIG. 4 is a front elevational view of the sheath body with the blade support being partly pulled out.

As illustrated in FIG. 3 and FIG. 4, when the push button 3 is pushed upward, the push button 3 brings the positioning element 4 to move upward and the position element 4 moves out from the positioning groove 6. The blade support 2 follows and moves out to the opening of the sheath body 1. The positioning lobe 10 on the top of the blade support 2 moves along the positioning channel 9 on the top of the sheath body 1, and is locked at the upper opening of the sheath body 1. The positioning element 4 is locked at the lower opening of the sheath body 1, thereby preventing the blade support 2 from falling out from the sheath body 1.

Following the movement of the blade support 2, the trapezoidal piece 21 of the blade support 2 moves. When the blade support 2 is drawn out of the sheath body 1, the trapezoidal piece 21 presses the second reset spring 51 downward, and the trapezoidal piece 21 follows the end of the second reset spring 51 and becomes slanting. The blade support 2 slides out along the lower part of the sheath body 1 because of slanting, and the knife blade is released from the knife sheath.

After the knife has been pulled out, the blade support 2 is pushed back into the sheath body 1. At this time, the positioning element 4 moves along the slanting surface of the guiding piece 8 with the wedge-like surface. When the positioning element 4 moves to the positioning groove 6, it falls into the positioning groove 6, and the blade support 2 restores to its original position.

When the knife has to be inserted into the knife sheath, the blade support 2 is drawn out, and at this time the trapezoidal piece 21 moves in the direction following the movement of the blade support 2, and the knife is put onto the blade support 2 and is being pushed into the sheath body 1. The blade support 2 and the trapezoidal piece 21 slide in together along with the second reset spring 51, and thus the knife is safely inserted into the sheath body 1.

Figure 5:
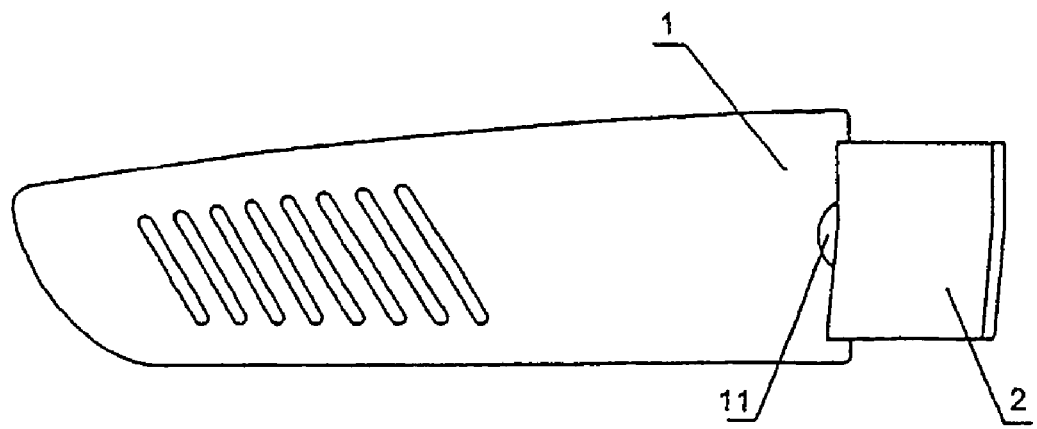
FIG. 5 is a rear elevational view of the sheath body with the blade support being partly pulled out.
Figure 6:
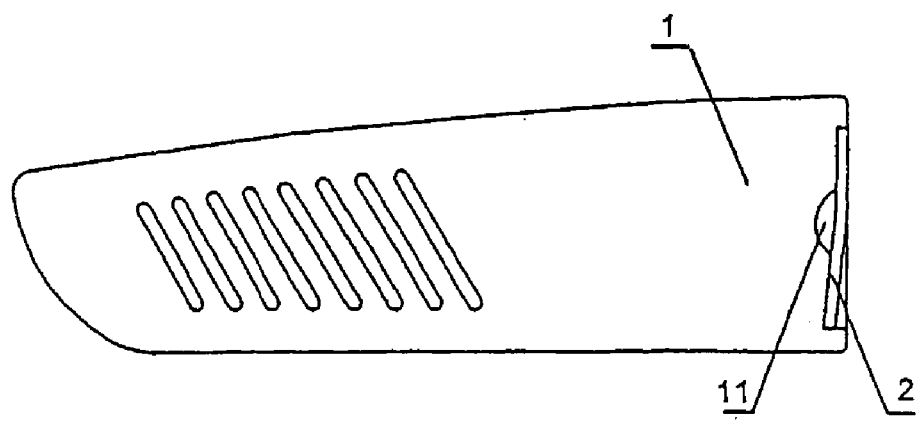
FIG. 6 is a perspective view of the present invention showing the rear view of the sheath body with the blade support completely inserted therein.
Figure 7:
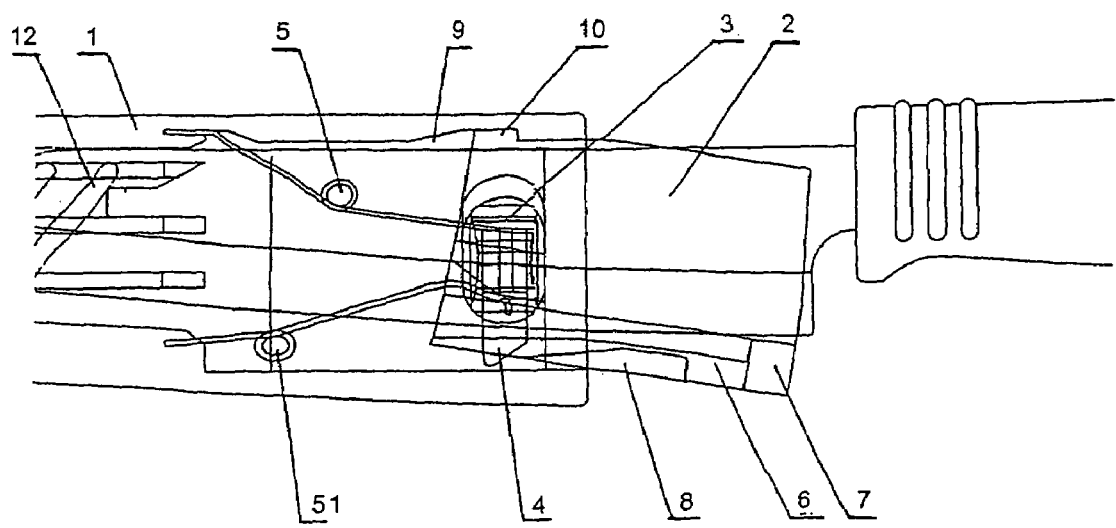
FIG. 7 is a schematic view of the present invention showing the connection of the blade support and the positioning element.

As illustrated in FIG. 5 and FIG. 6, a semi-circular notch 11 is disposed at the back in the middle of the opening of the sheath body 1.

What is claimed is:

1. A safe knife sheath comprising a sheath body and a blade support; the blade support is mounted inside the sheath body and movable in a sliding motion; a front part of the sheath body has a push button; a lower part of the push button is connected to a positioning element; a lower part of the blade support has a positioning groove corresponding to the positioning element; a positioning channel is disposed near an upper inner surface of the sheath body; on a top near an inner end of the blade support a positioning lobe corresponding to the positioning channel is disposed so that the blade support is prevented from being pulled out from the knife sheath when the positioning lobe reaches an outer end of the positioning channel; a top of the push button is connected to one end of a first reset spring, and the other end of the first reset spring is fixed in the upper end of the sheath body; in the back of the blade support a trapezoidal piece is disposed; the trapezoidal piece is in trapezoid shape with a bottom side, a top side, a first slanted side and a second slanted side; the bottom side which is parallel to the top side is shorter than the top side; the first slanted side is disposed further away from an inner end of the blade support; the second slanted side is disposed nearer to the inner end of the blade support; on the lower side of the trapezoidal piece a second reset spring is disposed; the second reset spring is a torsion spring with a first leg and a second leg; the first leg is fixed in a lower end of the sheath body; the second leg of the second reset spring is in an inverted V shape skewed towards an outer end of the sheath body so that the outer end of the second leg bends downwards; and the second leg is fixed on an inner side of the sheath body; the second slanted side of the trapezoidal piece substantially abuts against the outer end of the second leg when the blade support is at a position when the positioning lobe reaches the outer end of the positioning channel.

2. A safe knife sheath as in claim 1, wherein the lower part of the positioning element is in wedge shape.

3. A safe knife sheath as in claim 1, wherein the positioning groove comprises a locating piece and a guiding piece with a surface in a surface in wedge shape and the locating piece is disposed in the lower part of the blade support in position corresponding to an opening of the sheath body, and the guiding piece with the surface in wedge shape is disposed in the middle lower part of the blade support.

4. A safe knife sheath as in claim 1, wherein a semi-circular notch is disposed in a rear part of the sheath body, and the semi-circular notch is disposed in a middle of the opening of the sheath body.

5. A safe knife sheath as in claim 1, wherein a plurality of holes are perforated in the front part of the sheath body.

6. A safe knife sheath as in claim 5, wherein the plurality of holes are elongated holes.

\* \* \* \* \*